(12) United States Patent
Selcuk et al.

(10) Patent No.: US 8,476,344 B2
(45) Date of Patent: Jul. 2, 2013

(54) METHOD FOR PREPARING SILICON-SULFUR COMPOUNDS AND THEIR USE IN BITIMINOUS COMPOSITIONS

(75) Inventors: Sibel Selcuk, Westfield, IN (US); Perry Eyster, Brownsburg, IN (US)

(73) Assignee: Heritage Environmental Services, LLC, Indianapolis, IN (US)

( * ) Notice: Subject to any disclaimer, the term of this patent is extended or adjusted under 35 U.S.C. 154(b) by 271 days.

(21) Appl. No.: 12/856,807

(22) Filed: Aug. 16, 2010

(65) Prior Publication Data

US 2011/0046273 A1 Feb. 24, 2011

Related U.S. Application Data

(60) Provisional application No. 61/234,793, filed on Aug. 18, 2009.

(51) Int. Cl.
- C08L 95/00 (2006.01)
- C08L 27/22 (2006.01)
- C08L 27/24 (2006.01)
- C10C 3/02 (2006.01)

(52) U.S. Cl.
USPC .................. 524/59; 524/62; 524/64; 524/69; 106/273.1; 106/278; 523/205

(58) Field of Classification Search
USPC . 524/59, 62, 64, 69; 106/273.1, 278; 523/205
See application file for complete search history.

(56) References Cited

U.S. PATENT DOCUMENTS

| | | | |
|---|---|---|---|
| 2,567,724 A | 9/1951 | Moody | |
| 3,849,471 A | 11/1974 | Omietanski et al. | |
| 4,125,552 A | 11/1978 | Speier | |
| 4,376,830 A | 3/1983 | Nimer et al. | |
| 5,399,739 A * | 3/1995 | French et al. | 556/427 |
| 6,344,578 B1 | 2/2002 | Mautner et al. | |
| 6,472,481 B1 | 10/2002 | Luginsland et al. | |

FOREIGN PATENT DOCUMENTS

| JP | 08311349 A | 11/1996 |
|---|---|---|
| WO | WO 2008/148804 A1 | 12/2008 |

OTHER PUBLICATIONS

Anderson, Kurt E., Mar. 2000, "Recovery of Valuable Chlorosilane Intermediates by a Novel Waste Conversion Process", obtained at the internet address: http://www.osti.gov/bridge/purl.cover.jsp;jsessionid=C4D2A29A579C326BC6FEB2063831313F?purl=/795522-82wKri/webviewable/; retrieved on Dec. 27, 2010 (51 pgs).
Anonymous, "Waste", Wikipedia pp. 1-3, XP002615315, obtained at the internet address: http://en.wikipedia.org/wiki/Waste, retrieved on Dec. 27, 2010 (5 pgs.).
Zhang, Ning et al., "Conversion of a Direct Process High-Boiling Residue to Monosilanes by a Two-Step Catalysis Approach", *Res Chem Intermed*. vol. 33, No. 7, 2007, (pp. 613-622).
European Search Report from corresponding EP application No. EP 10 172 920.0-2115 dated Jan. 28, 2011, 13 pgs.

* cited by examiner

*Primary Examiner* — James J Seidleck
*Assistant Examiner* — Deve E Valdez
(74) *Attorney, Agent, or Firm* — Brinks Hofer Gilson & Lione

(57) ABSTRACT

A method of producing sulfur modified organosilane compounds that can be used in asphalt binders which method involves: combining together an organosilane or mixtures of organosilanes, a sulfide, a halogen acceptor and solvent to form a reaction mixture; and allowing the organosilane to react with the sulfide in the presence of a halogen acceptor to produce a sulfur modified organosilane compound. The sulfur modified organosilane compound can be introduced into a polymer modified or unmodified asphalt binder in which the sulfur modified organosilane compound reacts with components in the asphalt mixture to form a modified asphalt. The organosilanes used to produce the sulfur modified organosilanes can be from a source of waste products (such as Direct Product Residue) in which case the waste products can be reused in asphalt binders.

12 Claims, No Drawings

METHOD FOR PREPARING SILICON-SULFUR COMPOUNDS AND THEIR USE IN BITIMINOUS COMPOSITIONS

RELATED APPLICATION

This application is based upon U.S. Provisional Patent Application Ser. No. 61/234,793, filed Aug. 18, 2009 to which priority is claimed under 35 U.S.C. §120 and of which the entire specification is expressly incorporated herein by reference.

BACKGROUND

The present invention relates generally to a process for the production of sulfur containing organosilane compounds. The present invention further relates to a method of using sulfur containing organosilane compounds in bituminous compositions.

The composition of the invention can be broadly assigned to organic silicon containing compounds. More specifically, these reaction products are comprised of linear silicon-sulfur containing compounds, cyclic-organosilanes, silmethylenes, polycyclic silthaines, polysilthianes, cyclic and cluster silicon-sulfur compounds, and their mixtures.

Numerous methods have been disclosed in the art for the preparation of sulfur containing organosilicon compounds. U.S. Pat. No. 2,567,724 to Moody discloses a process for making polysilthianes consisting of hexamethyl cyclotrisilthiane and tetraphenyl cyclotristhiane. U.S Patent No. 2,590,039 to Richter et al. discloses the reaction of organosilicon halides with organo-dithiols. U.S. Pat. No. 6,472,481 to Luginsland et al. discloses a process for making linear polyorganosiloxanes. U.S. Pat. No. 6,211,345 to Weller et al. discloses a process for synthesizing sulfur-containing norborane silanes specifically. U.S. Pat. No. 6,384,256 to Backer discloses a process in which an alkali metal hydroxide compound reacts with a sulfide compound to form a polysulfide mixture and the subsequent reaction of polysulfides with a silane compound produces sulfur containing organosilicon compounds.

All the above patents involve the use of monosilanes or a single type of silane—or more specifically siloxanes.

Herzog et al. (2000, J. Organomet. Chem. V602, pg. 193-207) discusses the synthesis of cyclic silthianes using disilanes and two different types of silanes.

The "Direct Process" or "Rochow Process" refers to an indirect way of making the chlorosilanes from Me—Cl via the Grignard reagent RMgCl. This process is described by Rochow in U.S. Pat. No. 2,380,995 and in U.S. Pat. No. 2,488,487 by Barry et al. As a result of Direct Process several chlorosilane monomers and oligomers are produced in side reactions. The byproduct monomers typically consist of a mixture of methyltrichlorosilanes, trimethylcholorosilanes, and methydichlorosilanes. The oligomers include a high boiling blend of disilanes, silmethylenes and polysilalkylenes also known as "Direct Process Residue (DPR)." The high boiling fraction may also contain particulate silicon and metals or compounds thereof. The Direct Process generates one of the largest organosilane by-products streams.

Examples of sulfur containing organosilanes are found in U.S. Pat. No. 6,350,797 to Weller, U.S. Pat. No. 5,580,919 to Agostini et al. and U.S. Pat. No. 5,674,932 to Agostini et al. These compounds are utilized as additives and coupling agents, in rubber mixtures and tires to improve tread wear and better wet skid resistance on asphalt pavement surfaces.

Bituminous materials, sometimes referred as bitumen and also known as asphalt binder, is used as a binder in asphalts to pave roads and other surfaces and is used in other construction materials such as roofing materials, coatings, waterproofing applications, sealants, etc. Examples of bitumen that may be used in compositions and methods of present invention include natural bitumens, pyrobitumens, and artificial bitumens. Bitumens that are particularly preferred are those used for roadways, such as asphalt or malta.

Asphalt binders are frequently used in applications where there can be a wide variation in environmental conditions, particularly in temperature when used in pavement applications. Consequently the properties of asphalt binder in high and low temperature conditions are a concern. Asphalt gets hard and brittle at low temperatures, and becomes soft at higher temperatures. More specifically, in hot conditions/climates or under sustained loads, such as slow traffic or parked heavy loads, asphalt binders behave like a viscous liquid. In cold conditions/climates or under rapidly-applied loads such as fast moving heavy loads, asphalt binders behave like an elastic solid. Under either condition, when subjected to excessively heavy loads such as heavy truck traffic, asphalt can become brittle and crack and rutted.

Resistance to fatigue and impact and the adherence of the asphalt binder to the aggregate are crucial in paving applications. Some asphalt binders may require a relatively elastic behavior, such as high traffic areas and high loads. Typically in order to improve their elastic properties polymer modifiers, sulfur crosslinkers, and other additives are used with asphalt binders.

The present invention provides a process for the production of sulfur containing organosilane compounds from disilanes, monosilanes, and mixtures thereof including by-products and waste streams.

Further the present invention provides for the use of sulfur containing organosilane compounds in asphalt compositions as additives and/or crosslinking agents.

BRIEF SUMMARY

According to various features, characteristics and embodiments of the present invention which will become apparent as the description thereof proceeds, the present invention provides a method of producing a polymer-modified asphalt composition which method involves the steps of:

a) combining together an organosilane, or a mixture of organosilanes, a sulfide, a halogen acceptor, a suitable solvent to form a reaction mixture;

b) allowing the organosilane to react with the sulfide in the presence of a halogen acceptor to generate the sulfur containing organosilane; and c) introducing the sulfur containing organosilane to an asphalt binder as an additive and/or as a crosslinking agent.

The present invention further provides a polymer-modified asphalt composition produced by the steps of:

a) combining together an organosilane or a mixture of organosilanes, a sulfide, a halogen acceptor, a suitable solvent to form a reaction mixture;

b) allowing the organosilane to react with the sulfide in the presence of a halogen acceptor to generate the sulfur containing organosilane; and d) applying the sulfur containing organosilane to a polymer modified asphalt binder as an additive and/or a crosslinking agent.

The present invention also provides an asphalt composition that comprises a sulfur containing organosilane compound as a binder and/or as a crosslinking agent.

The present invention also provides a method of reusing organosilane waste products which involves:
  providing a source of waste organosilanes; and
  reacting the organosilanes with sulfide to generate sulfur containing organosilanes.

DETAILED DESCRIPTION OF THE PRESENTLY PREFERRED EMBODIMENTS

The present invention is directed to the use of organic silicon compounds and particularly chlorodisilanes and silmethylenes and the mixtures thereof as process feed materials. In particular the present invention is directed to asphalt compositions (inclusive of asphalt binders or asphalt binder compositions), including compositions that can be used to pave roads and other surfaces and can be used in other construction materials such as roofing materials, coatings, waterproofing applications, sealants, etc., which incorporate therein products from the reaction of organosilanes with sulfides in the presence of a halogen acceptor such as amines. The present invention is further directed to methods of producing polymer modified asphalt compositions. Reference herein to organic silicon compounds is intended to encompass, without limitation, organosilane compounds which may contain atoms other than silicon and hydrogen, including as non-limiting examples oxygen or nitrogen atoms.

The present invention provides a process for producing sulfur containing organosilane compounds, specifically cyclic and polycyclic silthianes that have particular use in asphalt compositions as an additive and/or crosslinking agent.

The present invention also provides asphalt compositions where organosilanes and organosilane by-products are utilized in the process of making sulfur containing or sulfur functionalized organosilanes.

The organosilanes and organosilane by-products utilized in this patent have the following general formula:

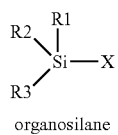

organosilane in which X can be halogens-more preferably chloride, R1, R2, and/or R3 can be any of the following groups: hydrogen, oxygen, alkoxy group of 1-8 carbon atoms, cycloalkoxy group, straight or branched chain alkoxy mercapto groups, alkyl group of 1-4 carbon atoms, phenyl, vinyl, amine, epoxy, another silane, siloxane, and silicon containing group.

According to one aspect the present invention is based on the use of organosilanes as a vehicle for the introduction of cross-linking and/or production of asphalt soluble silanes and siloxanes which improve the rheological properties of asphalt compositions.

During the course of the present invention it was discovered that when mixtures of organosilanes are reacted under the conditions defined by the present invention, asphalt soluble silicon-sulfur containing compounds are produced and confirmed to enhance the rheological properties of asphalt.

The present invention provides a way to reuse organosilanes and/or chlorosilane by-products which includes mixtures of chlorodisilanes and other components, including DPR. However, it is within the scope of the present invention to use specific chlorosilanes or mixtures of chlorosilanes such as, for example, trichlorosilane; organochlorosilanes, for example vinyltrichlorosilane, methyltrichlorosilane, methyldichlorosilane, dimethyldichlorosilane or methylvinyldichlorosilane or other chlorinated silanes and/or disilanes.

Whereas the disclosure of the invention depicts the addition of the organosilanes, sulfides, halogen acceptors reacted within the appropriate solvent, it is within the scope of this invention that the solvent can be the asphalt itself. It is also within the scope of the present invention to add the individual feed components in any combination. Also, experimentation has indicated that it is necessary to run the reaction and to introduce the product in dry environment.

It is also within the scope of the present invention to add one or more additional polymers to the reaction mixture including natural or synthetic rubbers, such as EPDM (ethylene-propylene-diene monomer), EPM (ethylene-propylene monomer), random styrene-butadiene copolymers such as SBR (styrene-butadiene rubber) or sequenced styrene-butadiene copolymers such as SBS (styrene-butadiene-styrene), linear or star copolymers, or SIS (styrene-isoprene-styrene), polyisobutylene (butyl rubber), polybutadiene, polyisoprene, polynorbornene, polychloroprene, polyvinyl chloride, ethylene-vinyl acetate copolymers and the like.

Features and characteristics of the present invention will be demonstrated in the following non-limiting examples.

Unless otherwise noted the reaction setup was essentially same for the reactions carried out below in each example. The reaction apparatus consisted of a 500 mL test tube reaction vessel equipped with a gas inlet tube and a condenser. The surface area and length of the reaction vessel proved most efficient in low-temperature condensation of the hydrogen sulfide gas during the tests. The glass tube, through which the gas was delivered, was fitted with an aerator to assist in diffusion and condensation of the hydrogen sulfide. A nitrogen blanket was maintained throughout the reaction. Off-gasses passed through a toluene filled impinger to maintain a closed system and assist in monitoring gas flows. The reactor was placed in a Dewar filled with dry ice and acetone to maintain low-temperature for the reaction.

Unless otherwise noted asphalt binder compositions were prepared by employing the following method. A quart can container was charged 500 grams of asphalt binder which was preheated to 163° C. The asphalt binder was obtained from BP (Whiting, Ind.) and had a PG rating of 64-22 per AASHTO M320. Using a quart can heater, the asphalt binder was heated to 190° C. and sheared with a Silverson high shear mixer at which time 1.5% unsaturated polymer (polymer ID: LCY 3411) was introduced by direct addition. The polymer modified asphalt was sheared for 10 minutes and the silicon sulfur compounds (see Table 1 for wt %) were also introduced by direct addition. The sample within the container continued to shear for 30 minutes. A lid was loosely placed on the container and the container was placed in an oven set at 163° C. for 18 hours. Upon the removal of the container from the oven and removal of the lid, any skim layer present was removed. The sample was then stirred and poured through a 20 mesh screen and the screened material was used for preparing the test samples.

EXAMPLE 1

Prior to immersion in the dry ice bath, the reactor was charged with 300mL of toluene, 50 mL of waste chlorosilane mixture, or Direct Process Residue (DPR). Using a 50 mL pipette, 47 mL of triethylamine was quickly introduced below the liquid line. The vapor from the chlorosilanes and the triethylamine react to form white webbing in the vapor space, therefore care was taken to minimize this product. The contents of the reaction vessel were brought to −90° C. by inserting the reactor into the dry ice-acetone mixture. During this time a small stream of nitrogen gas bubbled through the reactor to both provide an inert system and to provide agitation to its contents. After 30 minutes, anhydrous hydrogen sulfide was bubbled slowly into the mixture with the nitrogen. The reaction vessel was kept saturated with hydrogen sulfide until at least 100g $H_2S$ is delivered. The reactor remained in the low temperature bath, agitated by bubbling nitrogen gas stream, to ensure complete reaction. After a period of several hours, the reactor was slowly removed from the bath to prevent sudden vaporization of excess hydrogen sulfide. Nitrogen gas continued to blanket the reactor and carry the evolving gases through the impinger.

The contents of the reactor were vacuum filtered under nitrogen and rinsed three times with 50 mL of toluene. For this example the mass of the dried filter cake was found to be 53.9 grams. The filtrate was distilled to remove the toluene and any residual silane. The residue from this distillation was clear yellow low viscosity fluid. NMR analysis confirmed the presence of a mixture of silicon-sulfur compounds in the final product.

Experimental Sample 1 was prepared by the addition of the clear yellow fluid into the asphalt binder composition by following the protocol described above for the preparation of the asphalt binder compositions.

EXAMPLE 2

Example 2 was prepared by the same setup and in the same manner as Example 1 above except that the starting chlorosilane mixture was a purified form of Direct Process Residue obtained from Dow Corning. The final residue obtained from the distillation was a light tan, viscous liquid. NMR analysis confirmed the presence of a mixture of silicon-sulfur compounds in the final product.

Experimental Sample 2 was prepared by the addition of the light tan fluid into the asphalt binder composition by following the protocol defined above for the preparation of the asphalt binder compositions.

EXAMPLE 3

Example 3 was prepared using the same setup and the same procedure as Example 1 above except that the starting chlorosilane mixture was a tetrachlorosilane obtained from Dow Corning. The final residue obtained from the distillation was a clear yellow, low viscosity fluid. NMR analysis confirmed the presence of a mixture of silicon-sulfur compounds in the final product.

Experimental Sample 3 was prepared by the addition of the clear fluid into the asphalt binder composition by following the protocol discussed above for the preparation of the asphalt binder compositions.

EXAMPLE 4

Example 4 was prepared using the same setup and the same procedure as described above in reference to Example 1 except that the starting chlorosilane mixture was a methyltrichlorosilane obtained from Dow Corning. The final residue obtained from the distillation were fine white crystals. NMR analysis confirmed the presence of a mixture of silicon-sulfur compounds in the final product.

Experimental Sample 4 was prepared by the addition of the white crystals into the asphalt binder composition by following the protocol described above for the preparation of the asphalt binder compositions.

Control Samples

Experimental Samples 5 and 6 were prepared as controls to demonstrate the enhancing effect of silicon-sulfur compounds in bituminous compositions.

Sample 5 was prepared by using only the polymer modified asphalt binder. Sample 6 was prepared by using the neat asphalt binder with no additives.

The test samples and control samples were tested for Original Fail Temperature, Phase Angle (at 76° C.), RTFO Fail Temperature, RTFO Plastic Recovery, Separation and Softening Point using standardized test methods. The results of these tests are provided in the following Table.

TABLE

| | | Sample ID | | | | Control | |
|---|---|---|---|---|---|---|---|
| | Test Method | 1 | 2 | 3 | 4 | 5 | 6 |
| % Polymer | | 1.5 | 1.5 | 1.5 | 1.5 | 1.5 | 0 |
| % Si—S | | 0.7 | 0.5 | 1 | 0.5 | 0 | 0 |
| Original Fail Temp. ° C. | AASHTO T315 | 76.3 | 76 | 73.9 | 75.5 | 70.8 | 65.9 |
| Phase Angle @ 76° C. | AASHTO T315 | 83.8 | 84.1 | 85.7 | 79.6 | 86.8 | 87.7 |
| RTFO Fall Temp. ° C. | AASHTO T240/T315 | 73.4 | 74.1 | 73.9 | 73.5 | 71.9 | 65.7 |
| RTFO Elastic Recovery @ 25° C. | AASHTO T301 | 61 | 58 | 59 | 69 | 52.0 | 24.0 |
| Separation ° F. | ASTM D-7173 | 2 | 28 | 13.5 | — | 1.5 | 0 |
| Softening point ° F. | AASHTO T53 | 137 | 140 | 133.5 | 136 | 126.5 | 121 |

These results confirm the rheological properties of the asphalt compositions were improved by incorporating therein the silicon-sulfur compounds according to the present invention.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and set forth in the attached claims.

The invention claimed is:

1. A method of producing a polymer-modified asphalt composition which method involves the steps of:

a) combining together an organosilane, or a mixture of organosilanes, a sulfide, a halogen acceptor, a solvent to form a reaction mixture;
b) allowing the organosilane to react with the sulfide in the presence of a halogen acceptor to generate the sulfur containing organosilane; and
c) introducing the sulfur containing organosilane to an asphalt binder as an additive and/or as a crosslinking agent.

2. A method of producing a modified asphalt composition according to claim 1, wherein the modified asphalt has enhanced rheological properties.

3. A method of producing a modified asphalt composition according to claim 1, wherein the sulfur containing organosilane functions as a crosslinking agent in the asphalt binder.

4. A method of producing a modified asphalt composition according to claim 1, wherein the solvent is asphalt.

5. A method of producing a modified asphalt composition according to claim 1, where an additional crosslinking agent is added.

6. A method of producing a modified asphalt composition according to claim 1, which further comprises incorporating the modified asphalt composition into at least one of a pavement, a roofing material and a waterproofing composition.

7. A method of producing a modified asphalt composition according to claim 2, which further comprises incorporating the modified asphalt composition into at least one of a pavement, a roofing material and a waterproofing composition.

8. A method of producing a modified asphalt composition according to claim 3, which further comprises incorporating the modified asphalt composition into at least one of a pavement, a roofing material and a waterproofing composition.

9. A method of producing a modified asphalt composition according to claim 4, which further comprises incorporating the modified asphalt composition into at least one of a pavement, a roofing material and a waterproofing composition.

10. A method of producing a modified asphalt composition according to claim 5, which further comprises incorporating the modified asphalt composition into at least one of a pavement, a roofing material and a waterproofing composition.

11. A method of producing a modified asphalt composition according to claim 1 wherein the organosilane is obtained from a source of waste organosilanes.

12. A method of producing a modified asphalt composition according to claim 11, wherein the source of waste organosilanes comprises byproducts from a Direct Process for making chlorosilanes.

* * * * *